United States Patent
Wong et al.

(10) Patent No.: US 9,616,163 B2
(45) Date of Patent: Apr. 11, 2017

(54) METHOD AND SYSTEM OF ENHANCING REMOVAL OF TOXIC ANIONS AND ORGANIC SOLUTES IN SORBENT DIALYSIS

(71) Applicant: Fresenius Medical Care Holdings, Inc., Waltham, MA (US)

(72) Inventors: Raymond J. Wong, Norman, OK (US); Lucas Fontenelle, Oklahoma City, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 331 days.

(21) Appl. No.: 14/370,221

(22) PCT Filed: Dec. 31, 2012

(86) PCT No.: PCT/US2012/072256
§ 371 (c)(1),
(2) Date: Jul. 2, 2014

(87) PCT Pub. No.: WO2013/103607
PCT Pub. Date: Jul. 11, 2013

(65) Prior Publication Data
US 2015/0021271 A1  Jan. 22, 2015

Related U.S. Application Data

(60) Provisional application No. 61/582,850, filed on Jan. 4, 2012.

(51) Int. Cl.
A61M 1/16 (2006.01)
A61M 1/28 (2006.01)
(Continued)

(52) U.S. Cl.
CPC ............ *A61M 1/1696* (2013.01); *A61M 1/14* (2013.01); *A61M 1/28* (2013.01); *A61M 1/287* (2013.01);
(Continued)

(58) Field of Classification Search
CPC ...... A61M 1/1696; A61M 1/287; A61M 1/28; A61M 1/14; A61M 1/3472;
(Continued)

(56) References Cited

U.S. PATENT DOCUMENTS 6,960,179 B2 * 11/2005 Gura ................ A61M 1/16
                                                                 210/321.8
7,033,498 B2    4/2006 Wong
(Continued)

OTHER PUBLICATIONS

International Search Report and Written Opinion of the International Searching Authority issued in corresponding International Patent Application No. PCT/US2012/072256 dated Apr. 5, 2013 (9 pages).

*Primary Examiner* — John Kim
(74) *Attorney, Agent, or Firm* — Kilyk & Bowersox, P.L.L.C.

(57) ABSTRACT

A method of sorbent dialysis is provided for enhanced removal of uremic toxins, such as toxic anions and/or organic solutes, from spent dialysate. More highly adsorbable zirconium polymeric complexes of these anions and/or organic solutes can be initially formed in spent dialysate by treatment with zirconium salt solution or other zirconium cation source, and then removed with adsorbent to provide purified or regenerated dialysate. Sorbent dialysis systems for detoxifying spent dialysate containing toxic anions and organic solutes are also provided.

23 Claims, 2 Drawing Sheets

(51) Int. Cl.
*B01J 47/14* (2017.01)
*B01J 47/02* (2017.01)
*B01J 39/08* (2017.01)
*B01J 41/10* (2006.01)
*B01J 45/00* (2006.01)
*B01J 20/02* (2006.01)
*B01J 39/10* (2006.01)
*B01J 41/18* (2017.01)
*A61M 1/14* (2006.01)
*B01J 47/04* (2006.01)
*A61M 1/34* (2006.01)
*B01J 20/28* (2006.01)
*B01J 20/32* (2006.01)
*B01J 20/06* (2006.01)
*B01J 47/024* (2017.01)
*B01J 47/026* (2017.01)
*B01J 39/09* (2017.01)
*B01J 47/014* (2017.01)

(52) U.S. Cl.
CPC ........ *A61M 1/3472* (2013.01); *B01J 20/0211* (2013.01); *B01J 20/0292* (2013.01); *B01J 20/06* (2013.01); *B01J 20/28052* (2013.01); *B01J 20/3234* (2013.01); *B01J 39/09* (2017.01); *B01J 39/10* (2013.01); *B01J 41/10* (2013.01); *B01J 41/18* (2013.01); *B01J 45/00* (2013.01); *B01J 47/014* (2017.01); *B01J 47/024* (2013.01); *B01J 47/026* (2013.01); *B01J 47/04* (2013.01); *A61M 2202/0496* (2013.01); *A61M 2209/088* (2013.01); *B01J 2220/42* (2013.01); *B01J 2220/62* (2013.01)

(58) Field of Classification Search
CPC ...... A61M 2209/088; A61M 2202/0498; B01J 41/10; B01J 41/18; B01J 20/0211; B01J 20/0292; B01J 20/28052; B01J 20/06; B01J 20/3234; B01J 2220/42; B01J 2220/62; B01J 47/003; B01J 47/04; B01J 47/024; B01J 47/026; B01J 39/085; B01J 39/10; B01J 45/00; B01J 39/09; B01J 47/014

See application file for complete search history.

(56) References Cited

U.S. PATENT DOCUMENTS

| | | | |
|---|---|---|---|
| 8,409,444 B2* | 4/2013 | Wong | A61M 1/1696 210/483 |
| 2004/0099593 A1 | 5/2004 | De Paolis et al. | |
| 2007/0213665 A1* | 9/2007 | Curtin | A61M 1/1696 604/131 |
| 2010/0114012 A1 | 5/2010 | Sandford et al. | |
| 2010/0184198 A1 | 7/2010 | Joseph et al. | |
| 2010/0276374 A1* | 11/2010 | Kolb | B82Y 30/00 210/681 |
| 2014/0336568 A1* | 11/2014 | Wong | A61M 1/1696 604/29 |

* cited by examiner

METHOD AND SYSTEM OF ENHANCING REMOVAL OF TOXIC ANIONS AND ORGANIC SOLUTES IN SORBENT DIALYSIS

This application claims the benefit under 35 U.S.C. §119 (e) of prior U.S. Provisional Patent Application No. 61/582,850, filed Jan. 4, 2012, which is incorporated in its entirety by reference herein.

FIELD OF THE INVENTION

The present invention generally relates to the field of sorbent dialysis, and more specifically to a method and system of sorbent dialysis which can efficiently remove toxic anions and organic solutes from spent dialysate.

BACKGROUND OF THE INVENTION

Kidney failure can cause accumulation in body fluids, such as blood, of toxins and derivatives and metabolites of organic drugs taken by the patient. Sorbent dialysis systems provide treatment for patients with acute or chronic kidney disease. Dialysate is delivered to a dialyzer in prescribed amounts to cleanse the blood of impurities, correct the patient's body chemistry, and remove excess fluid. In sorbent dialysis, a sorbent cartridge can purify the initial dialysate and continuously regenerate spent dialysate throughout the treatment. Closed loop multi-pass sorbent based dialysis systems, for example, regenerate dialysate for reuse by passing spent dialysate through a regeneration section comprising a plurality of sorbent cartridges and suitable additives. Spent dialysate comprising urea, which is diffused from impure blood in the dialyzer, passes through sorbent cartridges. The sorbent cartridges bind uremic wastes, and also can be used for other tasks, such as balancing dialysate pH. A typical sorbent cartridge system comprises, for example, an enzyme layer consisting of urease, a cation exchange layer consisting of zirconium phosphate, an anion exchange layer consisting of hydrous zirconium oxide (HZO), and an adsorbent layer consisting of activated carbon. The REDY™ (REgenerative DialYsis) System is an example of a commercially available sorbent cartridge system which uses a similar arrangement of sorbents. During regenerative dialysis, the used or spent dialysate moves up through the layers of the cartridge. The enzymatic urease converts urea into ammonium carbonate. The ammonia and ammonium ions are then removed by the zirconium phosphate in exchange for $H^+$ and $Na^+$ ions. The carbonate from the urea hydrolysis then combines with $H^+$ to form bicarbonate ($HCO_3^-$) and carbonic acid ($H_2CO_3$). Carbonic acid is an unstable organic acid; most of it rapidly breaks down into water and carbon dioxide molecules ($CO_2$). The HZO (e.g., containing acetate as a counter ion) removes $HCO_3^-$, $P^-$, and other anions (e.g., $F^-$ in water), and releases acetate. The activated carbon absorbs organic metabolites such as creatine, uric acid, and nitrogenous metabolic waste of the patient as well as chlorine and chloramines from the water. The $CO_2$ gas bubbles are vented from the cartridge.

The present investigators have recognized that conventional sorbent dialysis can be inadequate to remove uremic toxins which include anions, organic solutes, or both. The present investigators further have recognized that HZO used as a clinical sorbent for some sorbent dialysis to remove phosphate from patients with renal diseases has limited adsorption capacity for uremic toxins such as sulfate and other toxic anions as well as organic solutes in spent dialysate, especially in the presence of phosphate.

SUMMARY OF THE INVENTION

A feature of the present invention is to provide a method of detoxifying spent dialysate containing toxin species comprising anions, organic solutes, or both.

Another feature of the present invention is to provide a method to detoxify spent dialysate wherein zirconium polymeric complexes of toxic anions, organic solutes, or both can be initially formed in spent dialysate and then removed with adsorbent to provide purified or regenerated dialysate.

A further feature of the present invention is to provide a dialysis system for conducting dialysis comprising a dialyzer in fluid communication with at least one treatment station wherein toxic anions, organic solutes, or both in spent dialysate can be converted to more highly adsorbable complex forms for removal before recirculating the resulting regenerated dialysate back to the dialyzer.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates in part to a method of detoxifying spent dialysate comprising: (a) providing a first spent dialysate comprising complexable species comprising complexable anions or complexable organic solutes or both; (b) converting the complexable species in the first spent dialysate to an adsorbable zirconium complex of the species to produce a second spent dialysate comprising the adsorbable zirconium complex of the species; and (c) passing the second spent dialysate through an ion exchange column comprising an ion exchange sorbent effective for adsorbing at least part of the zirconium complex of the species from the second spent dialysate to produce a third spent or regenerated dialysate having reduced content of the zirconium complex of the species than in the second spent dialysate.

The present invention further relates to an apparatus for conducting dialysis comprising: a dialyzer in fluid communication with at least one treatment station for passing a first spent dialysate to the at least one treatment station, wherein the first spent dialysate comprising complexable species comprising complexable anions or complexable organic solutes or both; the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with an ion exchange column for transmitting the second spent dialysate to the ion exchange column; and the ion exchange column comprising an ion exchange sorbent through which the second spent dialysate is passable effective for adsorbing at least part of the zirconium polymeric complex of the species from the second spent dialysate on the ion exchange sorbent to produce a third spent or regenerated dialysate having reduced content of the zirconium polymeric complex of the species than in the second spent dialysate, and wherein the ion exchange column further being in fluid communication with the dialyzer for recirculating at least a portion of the third spent or regenerated dialysate thereto.

The present invention further relates to a dialysis system comprising: a dialyzer in fluid communication with at least one treatment station for passing a first spent dialysate to the first treatment station, wherein the first spent dialysate comprising complexable species comprising at least one of complexable anions and complexable organic solutes; the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with a sorbent cartridge for passing the second spent dialysate to the sorbent cartridge; and the sorbent cartridge comprising an ion exchange sorbent through which the second spent dialysate is passable effective for adsorbing at least part of the zirconium polymeric complex of the species from the second spent dialysate to produce a third spent or regenerated dialysate having reduced content of the zirconium polymeric complex of the species than in the second spent dialysate, wherein the sorbent cartridge further being in fluid communication with the dialyzer for recirculating at least a portion of the third spent or regenerated dialysate thereto.

It is to be understood that both the foregoing general description and the following detailed description are exemplary and explanatory only and are only intended to provide a further explanation of the present invention, as claimed.

The accompanying drawings, which are incorporated in and constitute a part of this application, illustrate some of the embodiments and/or features of the present invention and together with the description, serve to explain the principles of the present invention. The drawings are not necessarily drawn to scale. Like numerals in the drawings refer to like elements in the various views.

DETAILED DESCRIPTION OF THE PRESENT INVENTION

Figure 1:
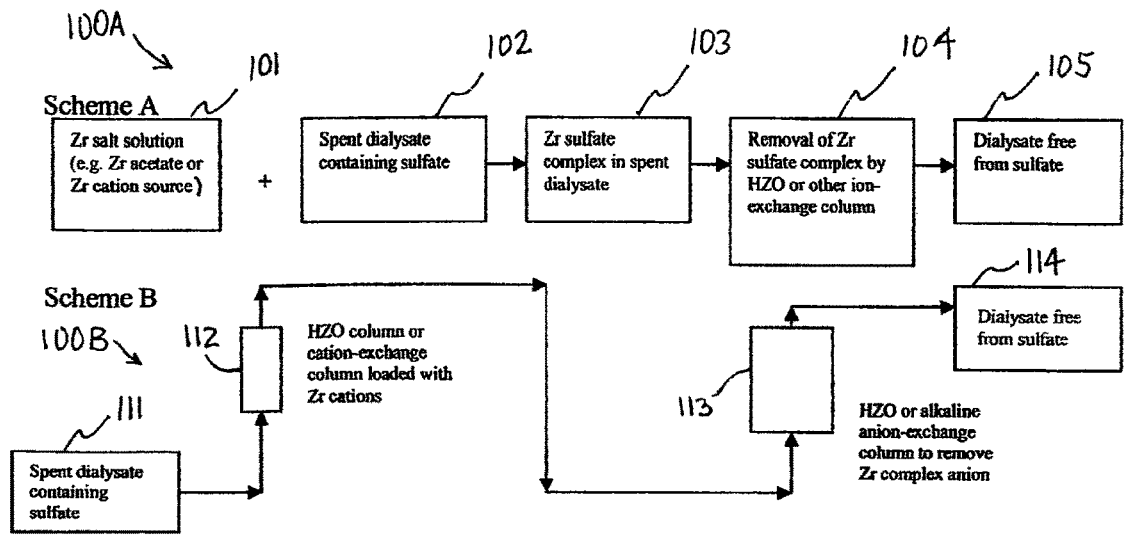
FIG. 1 shows a process flow diagram of sorbent dialysis methods according to Schemes A and B of examples of the present invention.

The present invention relates to providing enhanced removal of uremic toxins, such as toxic anions and/or organic solutes, from a patient for sorbent dialysis. In the present invention, zirconium polymeric complexes of these anions and/or organic solutes are initially formed in spent dialysate and then at least partially or fully removed with adsorbent to provide purified or regenerated dialysate. The formation of zirconium polymeric complex anions before adsorption can be provided by treating spent dialysate containing the toxins with a zirconium salt solution and/or other zirconium cation source to convert the toxins into a more highly adsorbable zirconium polymeric complex of the toxins. The treated dialysate containing the formed complex can then be passed through an ion exchange column having an ion exchange sorbent effective for adsorbing at least part or all of the zirconium polymeric complex of the toxins. This produces a regenerated dialysate having reduced content of the zirconium polymeric complex of the toxins, and hence a reduced level of the original toxins. The toxic anions and organic solutes can be referred to collectively herein as toxins or uremic toxins. The toxic anions which can be complexed and removed include, for example, sulfate, phosphate, oxalate, salicylate, citrate, phenolate, and the like, and any combinations thereof. The toxic organics which can be complexed and removed include, for example, phenol, ethylene glycol, ethanol, methanol, phenol barbital, and the like, and any combinations thereof. The removal efficiency of the indicated uremic toxins can be highly improved by a method of the present invention. The present invention also relates to dialysis systems which include dialysate regeneration components operable for converting uremic toxins in spent dialysate to more highly adsorbable complex forms thereof for removal from the spent dialysate. As described in more detail below, the present invention is useful in purifying or regenerating dialysate used in hemodialysis and in peritoneal dialysis. Conventional dialysis solutions for peritoneal dialysis or hemodialysis can be used and regenerated by the present invention and these solutions are known to those skilled in the art.

Hydrous zirconium oxide (HZO), for example, as used as clinical sorbent for sorbent dialysis to remove phosphate from a patient with renal disease has limited adsorption capacity for sulfate and other toxic anions (e.g., citrate, oxalate, and the like) as well as organic solutes in spent dialysate, especially in the presence of phosphate. For example, a HISORB+ cartridge for sorbent dialysis can contain HZO and SZC (sodium zirconium carbonate) as an anion exchanger to remove phosphate from a patient. Though the adsorption capacity of phosphate may be satisfactory, the removal of sulfate, for example, for treatment can be improved. The present invention relates in part to enhancing the removal efficiency of HZO and/or other sorbents for sulfate as well as other toxic anions and organic solutes by converting some or all of the sulfate and/or other anion or organic solute in spent dialysate to a more highly adsorbable zirconium polymeric complex form before adsorption by a HZO column and/or other sorbent column (e.g., an alkaline HZO column). The formation of the zirconium polymeric complex greatly enhances the affinity and selective adsorption of sulfate and/or other anion and/or organic solute by HZO and/or other anion exchanger material(s). The conversion of sulfate and/or other anion and/or organic solute to a more adsorbable zirconium polymeric complex form thereof can be achieved by loading a cation exchanger column or a HZO column with zirconium cations (e.g., in this example, HZO can serve as a cation carrier) and passing the spent dialysate through the column, or by adding a small amount of zirconium carboxylate solution to the anion or organic solute-containing spent dialysate. This technique may also be applied to improve the adsorption capacity of other protein bound organic uremic solutes by HZO by crosslinking the organic solutes to form a zirconium-organic complex before adsorption.

Further, a zirconium polymeric complex sulfate and/or other anion and/or solute can be formed by treating the spent dialysate containing sulfate and/or other anion and/or solute with a small amount of zirconium salt solution and/or zirconium cation at an appropriate pH. The appropriate pH can be neutral to acidic. The converting of the uremic toxins to the zirconium polymeric complex can be performed, for example, at a neutral to acidic pH. The pH can be, for example, from about 2 to about 7, or from about 3 to about 7, or from about 4 to about 7, or from about 4 to about 6, or other neutral to acidic pH values. As indicated, the zirconium cation source can be zirconium cations loaded or present on cation exchange sorbent (HZO and/or ZrP) column. The zirconium cation source can be provided in solution form by adding zirconium salt solution. The zirconium salt solution can be added to (or otherwise contacted with) spent dialysate in any suitable manner. For example, the zirconium salt solution can be added to spent dialysate by dropwise addition into a reservoir containing spent dialysate, and/or otherwise combining the zirconium salt solution with spent dialysate during re-circulation and before sorbent treatment. As indicated, the zirconium sulfate and/or other anion and/or solute complex in the spent dialysate formed can then be removed at least partially or completely by circulating the fluid through a column of alkaline HZO or HZO acetate or other ion exchange column (or any combination thereof), such as an anion exchange sorbent, which also can remove the residual zirconium.

A therapeutic value of a method for sorbent dialysis of the present invention can be to remove uremic toxins, such as toxic anions and/or organic solutes, from a uremic patient more effectively than possible with methods and systems which lack the toxin complexation step prior to treatment of the dialysate on an adsorbent. The method of the present invention can take advantage of zirconium ion characteristics, which can allow it to form a polymeric complex with oxygen-containing compounds. While not desiring to be bound to a specific theory, the zirconium cation can bind with the oxygen in the toxins and organic solutes to create a large complex that directly binds to the sorbents, and hence can increase the adsorption capacity significantly. Thus, the sorbent cartridge or device can have, for example, a layer(s) of cation exchange sorbent carrying the zirconium ion followed by a layer(s) of anion exchange sorbent to remove the zirconium complex anions. The conversion of the toxic anions to zirconium polymeric complex anions can be based on a special property of zirconium compounds by crosslinking with an immobilized zirconium cation column or by adding a small amount of zirconium salt solution to spent dialysate containing sulfate and/or other toxic anions to form the complex in a liquid medium comprising the spent dialysate itself. Further, the zirconium is generally non-toxic and can be mostly withheld by HZO, ZrP, and/or other ion exchange layer(s) used to remove the complex from the spent dialysate.

A column or sorbent cartridge including the indicated zirconium ion source and toxin adsorption column of the present invention as detailed herein also can be used to purify tap water or other water sources before the make up of dialysate for dialysis. Specifically, the zirconium ion source and toxin adsorption column detailed herein can be used for the adsorptive removal of sulfate (and/or other anions) from water before the makeup of dialysate and to reduce later desorption of sulfate by phosphate in spent dialysate when regenerated in the column in the presence of phosphate during dialysis.

The formation of Zr complex can greatly enhance the removal efficiency of toxic uremic anions or organic solutes by an adsorption column (e.g., HZO, alkaline HZO, anion-exchange, activated carbon, anion exchange resin, such as AMBERLITE™ XAD™, molecular sieve, alumina, and so forth). This advantage can reduce or remove a limitation of using HZO as a phosphate adsorbent alone for sorbent dialysis by remedying the deficiency of low adsorption capacity of the material for sulfate and organics. For example, HZO used in a column to purify water before the makeup of dialysate and to regenerate spent dialysate in the presence of phosphate for sorbent dialysis without pretreating the water or spent dialysate with the zirconium cation source to form the complex of a sulfate anion therein, can have a sulfate adsorption capacity of only about 4-6 mg per g HZO (or other amounts) in dialysate. By complexing the sulfate in water before the makeup of dialysate and in spent dialysate in the presence of phosphate prior to the HZO with a small amount of Zr cations followed by adsorption with HZO, such as in an example of the present invention, the sulfate adsorption capacity can be improved to about 10 mg per g HZO or higher, or 11 mg per g HZO or higher, or 12 mg per g HZO or higher, or 13 mg per g HZO or higher, or higher than about 14 mg sulfate per g HZO (or other per g of anion exchange material), and/or the capacity for phosphate can be about 7-8 mg phosphate-phosphorus combined per g HZO (or other amounts). In providing these sulfate adsorption capacities, the weight amount HZO used, for example, can approximately equal or exceed the weight amount of a Zr cation source (e.g., Zr ion loaded ZP) used as the cation source. For example, the HZO can be used in a weight amount which is at least 1.5 times greater, or at least 2 times greater, or from about 1.5 to about 2.5 times greater, than a weight amount of Zr ion loaded ZP used in the column. Increased amounts of the HZO relative to the amount of Zr ion loaded ZP used can reduce desorption of sulfate by phosphate during treatment of spent dialysate. The method of the present invention can be used in parallel with a sol gel HZO to enhance adsorption capacity of the zirconium complex furthermore by increasing the porosity and the BET surface area of the material.

By complexing the anion and/or organic solute toxins in spent dialysate before passing the spent dialysate through an adsorbent, at least 10%, at least 20%, at least 30%, at least 40%, or at least 50% more by weight of those toxic species in the original spent dialysate can be removed by the adsorbent than can be obtained for spent dialysate which does not receive the complexation treatment prior to treatment on the adsorbent. These removal amounts also can apply to removal of anions and/or organic solute toxins, such as sulfate, from water before the make up of dialysate. The removal amounts for the toxic species of anion and organic solutes indicated herein can apply individually to a specific species of toxin, or can apply to a combined or total toxic species amount in the spent dialysate. For example, a sulfate adsorption capacity of 14 mg per g adsorbent obtained for spent dialysate complexed and adsorbed by a method of the present invention as compared to a sulfate adsorption capacity of 4 mg per g adsorbent if the dialysate is not treated (complexed) according to the present invention, is a 250% or 2.5× by weight improvement (i.e., [14−4]/4×100). In other examples, by complexing the toxins before passing through an adsorbent, at least about 75% more by weight, or at least about 100% more by weight, or at least about 200% (about 2 times) more by weight, or at least about 300% (about 3 times) more by weight, or at least about 400% (about 4 times) more by weight, or at least about 500% (about 5 times) more by weight, or from about 50% to about 500% more by weight, or from about 75% to about 400% more by weight, or from about 100% to about 300% more by weight, of the toxic species in the original spent dialysate can be removed by the adsorbent than for spent dialysate which does not receive the complexation treatment. These removal amounts also can apply to removal of anions and/or organic solute toxins, such as sulfate, from water before the make up of dialysate.

Zirconium cations which can be used to form the zirconium polymeric complexes with the anion and/or organic solute can be, for example, carried by a chelating agent(s), such as EDTA loaded on HZO, a cation exchanger such as DOWEX™ series cation resin (Dow Chemical Company) or ZP, or can be in the form of free zirconium cation solution (e.g., zirconium carboxylate) added to the spent dialysate before entering the sorbent column. The complex formation using these zirconium cation sources typically can occur in a pH range, as indicated, of from about 2 to 7. The zirconium polymeric complex formed with these anions and/or organic solute can then be adsorbed completely by an anion exchange sorbent, such as HZO, anion exchange resin such as an AMBERLITE™ XAD™ series adsorbent resin (Dow Chemical Company), a molecular sieve, carbon (e.g., activated carbon), or alumina.

As indicated, a free zirconium ion source can be added to the spent dialysate before entering the column to form the zirconium polymeric complexes. The free zirconium ion source can be in the form of a dilute zirconium salt solution. The zirconium salt solution can comprise, for example, a zirconium carboxylate salt, such as zirconium acetate (e.g., $Zr^{x+}\cdot x\,CH_3COOH$). Zirconium acetate can be preferred to be used because of its low toxicity and because other zirconium carboxylate salts may be either insoluble in water or form a polymeric gel. The concentration of the zirconium carboxylate salt solution, such as zirconium acetate solution, used in the spent dialysate can be, for example, from about 0.025% to about 1% by weight based on dry weight of the added zirconium salt per total weight of the treated dialysate, or other values. Concentrations of zirconium acetate of less than about 0.1% by weight based on dry weight of the added zirconium salt per total weight of the treated dialysate, for example, from about 0.025% to about 0.09% or other values, can be sufficient to form the zirconium polymeric complexes. The solution forms of the zirconium cation can be combined with spent dialysate in any convenient manner, such as, for example, by adding dilute zirconium salt solution dropwise at the inlet of the indicated ion exchange column, or by adding the zirconium cation source solution to spent dialysate while temporarily held in a mixing vessel preceding the ion exchange column, or by in-line mixing such as by pumping the zirconium salt solution from a supply through a valved connector into a line through which the spent dialysate flows in communication with the ion exchange column. As an alternative, as indicated, the zirconium cation source can comprise an immobilized source such as a cation-exchange column or HZO column loaded with zirconium cations through which a spent dialysate can be passed to pick up zirconium cations for complexing with the toxic anions and organic solutes in the spent dialysate. For example, a column loaded with Zr cations through which the spent dialysate containing an anion or organic solute can be passed can comprise a zirconium sorbent material loaded with zirconium ions. The zirconium sorbent material can comprise hydrous zirconium oxide (HZO)(e.g., HZO.EDTA, NaHZO, HZO.acetate), or zirconium phosphate (ZrP)(e.g., sodium zirconium phosphate (NaZP), acid zirconium phosphate (AZP)), or any combination thereof. NaZP can refer to sodium zirconium phosphate or NaZrP, which can refer to the $Na^+$ form of zirconium phosphate (ZrP) or acid ZrP titrated by NaOH to a pH of from about 6.0 to about 7.4. NaZP can have chemical and physical properties, such as described in U.S. Patent Application Publication No. 2012/0234762 A1, which is incorporated in its entirety by reference herein. AZP can refer to the $H^+$ form of zirconium phosphate. AZP can have chemical and physical properties, such as described in U.S. Patent Application Publication Nos. 2010/0078387 A1 and 2012/0234762, which are incorporated in their entireties by reference herein.

In either mode of spent dialysate treatment used to convert the uremic toxins in the spent dialysate to a highly adsorbable zirconium polymeric complex thereof (e.g., Zr salt solution or Zr cation loaded column), a zirconium polymeric complex incorporating the uremic toxins is formed before the treated spent dialysate reaches a sorbent column. The zirconium polymer complex is removed from the spent dialysate at the sorbent column to provide a regenerated dialysate. As indicated, the ion exchange column used to adsorb the complex can be, for example, at least one of HZO, alkaline HZO, alkaline anion-exchange material, activated carbon, or any combinations of these.

FIG. 1 shows Schemes A and B which illustrate different ways of forming a zirconium polymeric complex of the uremic toxins before removing them from the dialysate with adsorbent according to a method of the present invention. In Scheme A, zirconium (Zr) salt solution 101 (e.g., a Zr acetate solution and/or other Zr cation source solution) is combined with spent dialysate 102 containing sulfate to form a Zr sulfate complex in the resulting second spent dialysate 103. The Zr sulfate complex can be removed from the spent dialysate by an HZO or other ion-exchange column 104 to provide a third spent or regenerated dialysate 105 which is free from sulfate or at least significantly reduced in sulfate compared to the original spent dialysate before treatment. These materials and results are illustrative and not limiting as other zirconium treatment salts and ion exchange columns can be used and other anions or organic solutes can be removed by the method.

In Scheme B shown in FIG. 1, spent dialysate 111 containing sulfate is passed through an HZO column or cation-exchange column 112 loaded with Zr cations. The column 112, loaded with zirconium cations, can contain a zirconium ion source prepared, for example, by soaking a zirconium sorbent in zirconium oxychloride (ZOC) solution, followed by filtration and drying to moist powder. The moisture level of the powder can be from about 20 to about 30 weight percent Loss on Drying (LOD). Other LODs are possible. The zirconium sorbent used for this treatment can be, for example, HZO.EDTA, NaHZO, HZO.acetate, NaZP, or any combinations thereof. As an example, Zr ion loaded zirconium phosphate (ZP) can be prepared by dissolving about 25-35 gm ZOC solid in about 175-225 ml deionized water. With agitation, about 80-120 gm NaZP powder can be added to the indicated ZOC solution with continued stirring for about 20-40 minutes. Chloride can be removed with filtering and washing, and the filter cake can be dried to about 20-30 wt % LOD to obtain the Zr ion loaded ZP. The Zr polymeric complex of sulfate and/or other anion and/or organic solute can be removed by HZO and/or other ion-exchange column 113 to provide dialysate 114 free from sulfate or at least significantly reduced in sulfate compared to the original spent dialysate before treatment. These materials and results are illustrative and not limiting as other ion exchange columns can be used and other anions or organic solutes can be removed by the method.

Figure 2:
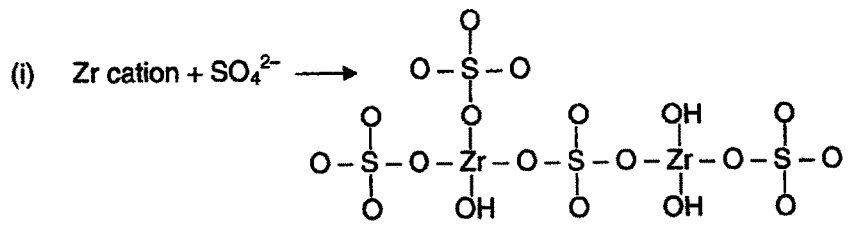
FIG. 2 shows reactions (i) and (ii) for forming complexes of uremic toxins in methods according to examples of the present invention.
Figure 2:

Reaction (i) in FIG. 2 shows an example of Zr cations complexed with sulfate ($SO_4^{-2}$) as a polymeric material. Reaction (ii) in FIG. 2 shows an example of Zr cations complexed with citrate or oxalate toxic species to form a zirconium polymeric complex thereof. In reaction (ii), the integers m and n represent positive integers that balance the compound, and R can be a hydrocarbon group, such as an alkyl group (e.g., methyl). As illustrated, for example, in reaction (i) of FIG. 2, the method of the present invention can make use of a property of Zr cations or salt solutions to crosslink or form polymeric complex anions with the anions or chelates with the organic solutes which are then easily removed by the HZO column or an alkaline anion column or carbon due to crosslinking and high affinity of these polymeric complex anions or chelates to the adsorbents. A zirconium cation or salt solution can form polymeric complexes or chelates with sulfate, citrate, oxalate, or the like, which may be noncrosslinked or linear polymers, such as illustrated in reaction (ii) in FIG. 2.

The indicated zirconium ion source and toxin adsorption column can be prepared as a separate column adjacent or adjunct to another sorbent cartridge for sorbent dialysis or can be directly incorporated into a single sorbent cartridge design with different materials in different layers. When the zirconium ion source is an immobilized zirconium cation column separate from a sorbent cartridge, the immobilized zirconium ion source material in the column preferably can be arranged as preceding a layer of anion exchange sorbents or resins for the adsorption of toxic anions like sulfate or oxalate in the same column, and preceding a layer of carbon or alumina for the adsorption of organic toxins like phenol in the same column, or both. If used as a separate adjunct column, the adjunct column can precede the sorbent cartridge in the fluid forward direction of the dialysate regeneration circuit. The composition and pH of the regenerated dialysate generally is not significantly affected after passing through a sequential arrangement of adjunct column and sorbent cartridge because a small column can be used for the toxic anion and organic removal and any small amount of Zr ion leakage can be totally removed by a succeeding sorbent cartridge.

As indicated, the ion exchange column or columns used for the adsorption of the zirconium polymeric complex anions and organic solutes can form part of a sorbent cartridge used to purify the spent dialysate before reuse in dialysis. Different sorbent materials can be arranged as different layers in the same sorbent cartridge. An appropriate combination of sorbents can be used, for example, to remove not only the zirconium polymeric complexes of anions and organic solutes, but also to remove nitrogenous waste products, such as uric acid, creatinine, and/or other nitrogenous metabolic waste of the patient, as well as chlorine and chloramines from the water, or make other purifications of the dialysate. Additional ion exchange adsorbent materials or other sorbent materials which can be combined with the ion exchange columns used for adsorbing the zirconium polymeric complex anions and organic solutes in the same or separate sorbent cartridge according to a method of the present invention can include, for example, the materials and cartridge arrangements shown in U.S. Patent Application Publication No. 2010/0078387 A1, which is incorporated in its entirety by reference herein. Chemical additives optionally can be added to the resulting regenerated dialysate before reuse in a dialyzer, such as to maintain the essential concentration of electrolytes and control acidosis or other metabolic disorders. The indicated zirconium ion source and toxin adsorption column of the present invention can be present as a layer (or layers) in sorbent cartridges such as those described in U.S. Pat. No. 7,033,498 B2, U.S. Pat. No. 6,878,283 B2, in Sorb Technology's REDY cartridge, and in SORB+/HD and HISORB+/HD Cartridges, all incorporated in their entirety by reference herein. When directly incorporated into a sorbent cartridge, such as a REDY cartridge or other cartridge, for example, from about 150-250 gm of Zr ion loaded ZP can precede from about 1200-1600 gm of ZP in the cartridge, and the activated carbon layer position can be changed from near the inlet of the cartridge to a position at the top of the cartridge and after a HZO layer, in the fluid flow direction.

Figure 3:
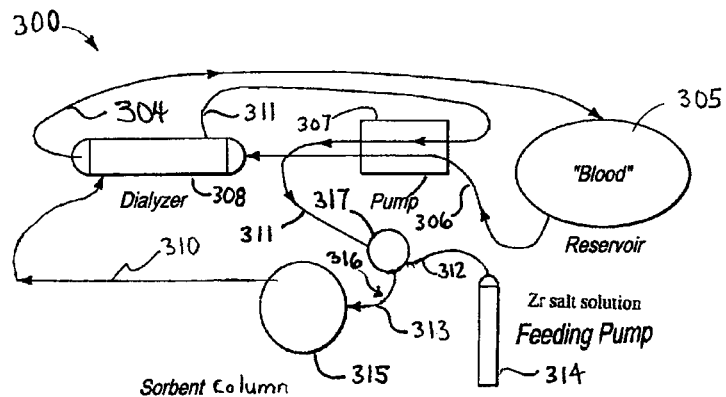
FIG. 3 shows a schematic illustration of a sorbent dialysis system according to an example of the present invention.

FIG. 3 shows a schematic illustration of a sorbent dialysis system 300 for performing dialysis according to an example of the present invention wherein a Zr salt solution 312 is combined with spent dialysate 311 containing complexable uremic toxic species comprising complexable anions and/or complexable organic solutes. For sake of this illustration, the toxic species which is complexed is referred to as an anion, but it is understood that it also may be a combination of different anions, or an organic solute individually or a combination of different organic solutes, or a combination of one or more types of anions and one or more types of organic solutes, in the spent dialysate. The spent dialysate 311 is discharged from dialyzer 308 for sorbent treatment before it is recirculated back to the dialyzer for reuse. The dialyzer 308 is in fluid communication with a treatment station 317 for passing the spent dialysate 311 containing the complexable anion or other complexable toxic species to the treatment station 317. Zr salt solution 312, for example, can be fed to the treatment station 317 where the Zr salt solution can be combined with the spent dialysate 311. A feeding pump 314 or other suitable introduction device can be used to feed the Zr salt solution to the treatment station 317. In the treatment station 317, the toxin species in the spent dialysate are combined with a zirconium salt solution and/or other zirconium cation source in solution form. The toxic species in the spent dialysate are converted to adsorbable zirconium polymeric complex anions to produce a second spent dialysate 313 which comprises an adsorbable zirconium polymeric complex of the toxic species. The treatment station 317 is in fluid communication with an ion exchange column 315 for transmitting the second spent dialysate 313 to the ion exchange column 315. The ion exchange column 315 can comprise an ion exchange sorbent (through which the second spent dialysate is passable) effective for adsorbing at least part of the zirconium polymeric complex of the toxic species from the second spent dialysate on the ion exchange sorbent to produce a third spent or regenerated dialysate 310. The regenerated dialysate 310 has a reduced content of the toxic species than in the spent dialysate 311. The ion exchange column 315 can be in fluid communication with the dialyzer 308 for recirculating at least a portion or all of the regenerated dialysate 310 thereto. A pump 307 can be used to pump blood 306 from the blood reservoir 305, e.g., a patient, and to pump spent dialysate 311 to the treatment station 317 and the ion exchange column 315 from there. Filtered blood 304 is circulated from the dialyzer 308 back to the reservoir 305. The system of FIG. 3 can be used, for example, to apply the method of Scheme A in FIG. 1.

Figure 4:
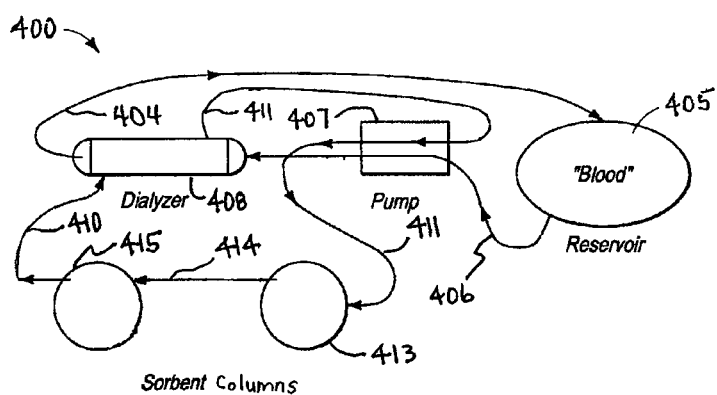
FIG. 4 shows a schematic illustration of a sorbent dialysis system according to another example of the present invention.

FIG. 4 shows a schematic illustration of a sorbent dialysis system 400 for performing dialysis according to an example of the present invention wherein a spent dialysate 411 containing complexable toxic anion and/or organic solute that is discharged from dialyzer 408 is passed through an HZO column or cation-exchange column loaded with Zr cations 413. A second spent dialysate 414 is formed containing Zr toxin anion complex or other complexed toxic species, which is discharged from column 413. The Zr toxin anion complex or other complexed toxic species in the spent dialysate 414 is removed by passing dialysate 414 through an HZO or other ion-exchange column 415 to provide dialysate 410 free from or at least in reduced amount of toxic anion and/or other complexed toxic species than in the original spent dialysate 411. The ion exchange column 415 can comprise an ion exchange sorbent (through which the spent dialysate is passable) effective for adsorbing at least part of the zirconium polymeric complex of the toxic species from the second spent dialysate 414 on the ion exchange sorbent to produce a third spent or regenerated dialysate 410 having reduced content of the toxin species than in the spent dialysate 411. The ion exchange column 415 can be in fluid communication with the dialyzer 408 for recirculating at least a portion of the regenerated dialysate thereto. A pump 407 can be used to pump blood 406 from the blood reservoir 405, e.g., a patient, and to pump spent dialysate 411 to the column 413 and column 415 from there. Filtered blood 404 is circulated from the dialyzer 408 back to the reservoir 405. The system of FIG. 4 can be used, for example, to apply the method of Scheme B in FIG. 1.

The present invention can be used to provide stationary sorbent dialysis systems or portable sorbent dialysis systems. The sorbent dialysis systems can include sorbent hemodialysis, a wearable artificial kidney, sorbent peritoneal dialysis, and other sorbent dialysis systems.

The present invention includes the following aspects/embodiments/features in any order and/or in any combination:

1. The present invention relates to a method of detoxifying spent dialysate comprising:
   (a) providing a first spent dialysate comprising complexable species (e.g., complexable toxic species) comprising complexable anions or complexable organic solutes or both;
   (b) converting the complexable species in the first spent dialysate to an adsorbable zirconium complex of the species to produce a second spent dialysate comprising the adsorbable zirconium complex of the species;
   (c) passing the second spent dialysate through an ion exchange column comprising an ion exchange sorbent effective for adsorbing at least part of the zirconium complex of the species from the second spent dialysate to produce a third spent dialysate having reduced content of the zirconium complex of the species than in the second spent dialysate.

2. The method of any preceding or following embodiment/feature/aspect, wherein the adsorbing is performed in the presence of phosphate ions in the second spent dialysate.

3. The method of any preceding or following embodiment/feature/aspect, wherein the species are anions.

4. The method of any preceding or following embodiment/feature/aspect, wherein the species are sulfate ions, citrate ions, oxalate ions, or phenolate ions, or any combinations thereof.

5. The method of any preceding or following embodiment/feature/aspect, wherein the species are at least one organic solute.

6. The method of any preceding or following embodiment/feature/aspect, wherein the converting of the species in the first spent dialysate to the zirconium complex comprises contacting the first spent dialysate with a zirconium salt solution or cation source.

7. The method of any preceding or following embodiment/feature/aspect, wherein the zirconium salt solution or cation source comprises a zirconium carboxylate salt.

8. The method of any preceding or following embodiment/feature/aspect, wherein the zirconium salt solution or cation source comprises zirconium acetate.

9. The method of any preceding or following embodiment/feature/aspect, wherein the zirconium salt solution or cation source comprises a cation exchange sorbent column comprising zirconium cations through which the first spent dialysate passes.

10. The method of claim 1, wherein the converting of the species in the first spent dialysate to the zirconium complex comprises contacting the first spent dialysate with hydrous zirconium oxide (HZO).

11. The method of any preceding or following embodiment/feature/aspect, wherein the zirconium salt solution or cation source comprises a column through which the first spent dialysate is passed, wherein the column comprising hydrous zirconium oxide (HZO), zirconium phosphate (ZrP), or both.

12. The method of any preceding or following embodiment/feature/aspect, wherein the converting is performed at a pH of from about 2 to about 7.

13. The method of any preceding or following embodiment/feature/aspect, wherein the adsorbing is effective to remove at least about 50% by weight of the zirconium complex of the species in the second spent dialysate.

14. The method of any preceding or following embodiment/feature/aspect, wherein the adsorbing is effective to remove from about 50% to about 500% by weight of the zirconium complex of the species in the second spent dialysate.

15. The method of any preceding or following embodiment/feature/aspect, wherein the ion exchange column is a cartridge comprising at least one of HZO, alkaline anion-exchange material, activated carbon, or any combinations of these layers.

16. The method of any preceding or following embodiment/feature/aspect, wherein the ion exchange column is a cartridge containing alkaline HZO.

17. The method of any preceding or following embodiment/feature/aspect, wherein the ion exchange column is a sorbent cartridge.

18. The method of any preceding or following embodiment/feature/aspect, wherein the ion exchange column is incorporated into a wearable artificial kidney.

19. The method of any preceding or following embodiment/feature/aspect, wherein a dialyzer is provided in fluid communication with at least one treatment station wherein the first spent dialysate passes from the dialyzer to the at least one treatment station where the converting of the species in the first spent dialysate to the adsorbable zirconium complex is provided to produce the second spent dialysate, and then passing the second spent dialysate through the ion exchange column comprising an ion exchange sorbent, wherein the ion exchange column further being in fluid communication with the dialyzer for recirculating at least a portion of the third spent dialysate thereto.

20. The method of any preceding or following embodiment/feature/aspect, wherein the first spent dialysate is spent hemodialysate, spent peritoneal dialysate, or combinations thereof.

21. The method of any preceding or following embodiment/feature/aspect, wherein the dialyzer is in fluid communication with blood of a patient.

22. The present invention further relates to an apparatus for conducting dialysis comprising: a dialyzer in fluid communication with at least one treatment station for passing a first spent dialysate to the at least one treatment station, wherein the first spent dialysate comprising complexable species (e.g., complexable toxic species) comprising complexable anions or complexable organic solutes or both;

the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with an ion exchange column for transmitting the second spend dialysate to the ion exchange column; and the ion exchange column comprising an ion exchange sorbent through which the second spent dialysate is passable effective for adsorbing at least part of the zirconium polymeric complex of the species from the second spent dialysate on the ion exchange sorbent to produce a third spent dialysate having reduced content of the zirconium polymeric complex of the species (e.g., toxic species) than in the second spent dialysate, and wherein the ion exchange column further being in fluid communication with the dialyzer for recirculating at least a portion of the third spent dialysate thereto.

23. The present invention further relates to a dialysis system comprising:

a dialyzer in fluid communication with at least one treatment station for passing a first spent dialysate to the first treatment station, wherein the first spent dialysate comprising complexable species (e.g., complexable toxic species) comprising at least one of complexable anions and complexable organic solutes;

the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with a sorbent cartridge for passing the second spent dialysate to the sorbent cartridge;

the sorbent cartridge comprising an ion exchange sorbent through which the second spent dialysate is passable effective for adsorbing at least part of the zirconium polymeric complex of the species from the second spent dialysate to produce a third spent dialysate having reduced content of the zirconium polymeric complex of the species than in the second spent dialysate, wherein the sorbent cartridge further being in fluid communication with the dialyzer for recirculating at least a portion of the third spent dialysate thereto.

24. The method, apparatus or system of any preceding or following embodiment/feature/aspect, wherein the species is phenol, ethylene glycol, ethanol, methanol, phenol barbital, or any combinations thereof.

25. The present invention further relates to a method of detoxifying spent dialysate comprising:

(a) providing a first spent dialysate comprising complexable species (e.g., complexable toxic species) comprising complexable anions and/or complexable organic solutes;

(b) converting at least a portion of the complexable species in the first spent dialysate to an adsorbable zirconium polymeric complex of said species to produce a second spent dialysate comprising the adsorbable zirconium polymeric complex of the species;

(c) passing the second spent dialysate through an ion exchange column comprising an ion exchange sorbent effective for adsorbing at least part of the zirconium polymeric complex of the species from the second spent dialysate to produce a regenerated dialysate having reduced content of the species than in the first spent dialysate.

26. The present invention further relates to an apparatus for conducting dialysis comprising:

a dialyzer in fluid communication with at least one treatment station for passing a first spent dialysate to the at least one treatment station, wherein the first spent dialysate comprising complexable species (e.g., complexable toxic species) comprising complexable anions and/or complexable organic solutes;

the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with an ion exchange column for transmitting the second spend dialysate to the ion exchange column; and the ion exchange column comprising an ion exchange sorbent, through which the second spent dialysate is passable, effective for adsorbing at least part of the zirconium polymeric complex of the species from the second spent dialysate on the ion exchange sorbent to produce a regenerated dialysate having reduced content of the species (e.g., toxic species) than in the first spent dialysate, and wherein the ion exchange column further being in fluid communication with the dialyzer for recirculating at least a portion of the regenerated dialysate thereto.

27. The present invention further relates to a dialysis system comprising: a dialyzer in fluid communication with at least one treatment station for passing a first spent dialysate to the first treatment station, wherein the first spent dialysate comprising complexable species (e.g., complexable toxic species) comprising complexable anions and/or complexable organic solutes;

the at least one treatment station capable of converting the species in the first spent dialysate to adsorbable zirconium polymeric complex anions to produce a second spent dialysate comprising adsorbable zirconium polymeric complex of the species, and the at least one treatment station in fluid communication with a sorbent cartridge for passing the second spent dialysate to the sorbent cartridge;

the sorbent cartridge comprising an ion exchange sorbent, through which the second spent dialysate is passable, effective for adsorbing at least part of the zirconium polymeric complex of the species from the second spent dialysate to produce a regenerated dialysate having reduced content of the toxic species than in the first spent dialysate, wherein the sorbent cartridge further being in fluid communication with the dialyzer for recirculating at least a portion of the regenerated dialysate thereto.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be only exemplary of the present invention. Unless indicated otherwise, all amounts, percentages, ratios and the like used herein are by weight.

EXAMPLES

Example 1

The anion adsorption capacity of a zirconium ion source and toxin adsorption column was tested in experiments which simulated the removal of sulfate from tap water before the make up of dialysate and determined if desorption of sulfate by phosphate in dialysate occurred subsequently during dialysis. A column without the zirconium ion source was tested for comparison.

The sulfate adsorption column test specifications used for these experiments were as follows:
Column size: 1 inch diameter column containing 20 gm of HZO with and without a Zr ion loaded preceding layer.
Flow rate: 10 ml per minute.
Initial water treatment: 1 L of tap water containing sulfate at 25 mg/dL or 250 ppm is treated by the column for sulfate removal.
Sequential treatment of dialysate:
2 L of dialysate containing 25 mEq/L NaHCO$_3$, 120 mEq/L NaCl, and 7.4 mg/dL PO$_4$-P was treated by the column for phosphate removal.

A single pass system was set up in which the tap water, and then the dialysate, was pumped through the column in a single pass mode at the indicated flow rate. Fluid samples at the column inlet side and effluent side were collected at different times while the tap water or dialysate was pumped through the column. Phosphate adsorption and sulfate desorption with respect to volume of dialysate treated were determined in these experiments. Additional testing details and results for the tested columns are as follows.

For a column (1) containing 20 gm HZO preceded by 10 gm Zr loaded ZP, the column first picked up all of the sulfate in the tap water (250 mg and more). There was total adsorption of phosphate and no desorption of sulfate by the phosphate throughout the 2 L dialysate treatment afterwards. Thus, adsorption capacity for sulfate in the presence of phosphate was 250 mg/20 gm HZO and more, and for phosphate, the capacity was 148 mg PO$_4$-P/20 gm HZO and more.

For a comparison, column (A) containing 20 gm HZO with no preceding Zr loaded ZP, the column only picked up about 120 mg sulfate in the tap water and the sulfate started to come out from the column after 500 ml of dialysate containing 7.4 mg/dL PO$_4$-P passed through the column (i.e. after 37 mgPO$_4$-P removal), although the column continued to remove the phosphate throughout the test. Thus, adsorption capacity for sulfate in the presence of phosphate was 120 mg/20 gm HZO and less, and for phosphate, the adsorption was similar to the column (1).

For a column (2) containing 10 gm HZO preceded by 10 gm Zr loaded HZO, the column first picked up all of the sulfate in the tap water (250 mg and more). There was total adsorption of phosphate from the dialysate like the first column (1), but desorption of sulfate by phosphate occurred after 1135 ml of dialysate passed through the column (i.e., after 84 mg PO$_4$-P removal).

Example 2

The anion adsorption capacity of a zirconium ion source and toxin adsorption column was tested on dialysate in experiments which used the following test specifications on a test system which was otherwise similar to that used for the experiments of Example 1. 2 L of the dialysate containing sulfate at 25 mg/dL was passed through a 2 inch diameter column containing 20 gm HZO.acetate (HZO.Ac) preceded by a layer of 10-20 gm Zr ion loaded ZP at the flow rate of 25 mL/minute. A column with the HZO.Ac and without the zirconium ion source was tested for comparison. Sulfate capacity was analyzed by the total amount of effluent with no detectable sulfate. Results of the experiments are shown in Table 1. In the table, "DL" refers to detection limit, and ICP" refers to Inductively coupled plasma atomic emission spectroscopy. In Test No. 8 of Table 1, no ZP loaded with Zr ion is used.

TABLE 1

| Test No. | Amount HZO.Ac | Amount Zr Ion Loaded ZP (AZP or NaZP) | Volume of Dialysate Treated Below DL of Sulfate | Adsorption of Sulfate by HZO.Ac | Zr ion leakage |
|---|---|---|---|---|---|
| 1 | 20 gm | None (control) | 600 mL | 150 mg/20 gm | <1 ppm DL (reagent) |
| 2 | 20 gm | 10 gm Zr ion/NaZP | 1000 mL | 250 mg/20 gm | <DL |
| 3 | 20 gm | 10 gm Zr ion/AZP | 1200 mL | 300 mg/20 gm | <DL |
| 4 | 20 gm | 20 gm Zr ion/NaZP | 1600 mL | 400 mg/20 gm | <DL |
| 5 | 20 gm | 20 gm Zr ion/AZP | 1600 mL | 400 mg/20 gm | <DL |
| 6 | 20 gm | 140 gm ZP pH 6.0/20 gm Zr ion/AZP | 1600 mL | 400 mg/20 gm | <DL |
| 7 | 20 gm | 140 gm ZP pH 6.0/20 gm Zr ion/NaZP | 1600 mL | 400 mg/20 gm | 0 ppm ICP |
| 8 | 20 gm | 160 gm ZP pH 6.0 and no Zr ion (control) | 700 mL | 175 mg/20 gm | 0 ppm ICP |

The results in Table 1 show that the adsorption capacity for sulfate is highly increased in the columns of Test Nos. 2-7 that included Zr ion loaded ZP in comparison to the controls of Test Nos. 1 and 8 that did have the Zr ion loaded ZP. Further, there was no detectible Zr ion leakage from the column in Test Nos. 2-7 even though the column contained Zr ion loaded ZP. The results of Test Nos. 7 and 8 show that a small amount of Zr ion loaded ZP (20 g as in Test No. 7) can effectively improve the sulfate capacity from 175 mg (Test No. 8) to 400 mg (Test No. 7) with no Zr ion leakage.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:
1. A method of detoxifying spent dialysate comprising:
   (a) providing a first spent dialysate comprising complexable species comprising complexable anions or complexable organic solutes or both;
   (b) converting the complexable species in said first spent dialysate to an adsorbable zirconium complex of said species to produce a second spent dialysate comprising said adsorbable zirconium complex of said species;

(c) passing said second spent dialysate through an ion exchange column comprising an ion exchange sorbent effective for adsorbing at least part of said zirconium complex of said species from said second spent dialysate to produce a third spent dialysate having reduced content of said zirconium complex of said species than in said second spent dialysate.

2. The method of claim 1, wherein said adsorbing is performed in the presence of phosphate ions in the second spent dialysate.

3. The method of claim 1, wherein said species are anions.

4. The method of claim 1, wherein said species are sulfate ions, citrate ions, oxalate ions, or phenolate ions, or any combination thereof.

5. The method of claim 1, wherein said species are at least one organic solute.

6. The method of claim 1, wherein said converting of species in said first spent dialysate to said zirconium complex comprises contacting said first spent dialysate with a zirconium salt solution or cation source.

7. The method of claim 6, wherein said zirconium salt solution or cation source comprises a zirconium carboxylate salt.

8. The method of claim 6, wherein said zirconium salt solution or cation source comprises zirconium acetate.

9. The method of claim 6, wherein said zirconium salt solution or cation source comprises a cation exchange sorbent column comprising zirconium cations through which said first spent dialysate passes.

10. The method of claim 1, wherein said converting of said species in said first spent dialysate to said zirconium complex comprises contacting said first spent dialysate with hydrous zirconium oxide (HZO).

11. The method of claim 6, wherein said zirconium salt solution or cation source comprises a column through which said first spent dialysate is passed, wherein said column comprising hydrous zirconium oxide (HZO), zirconium phosphate (ZrP), or both.

12. The method of claim 6, wherein said converting is performed at a pH of from about 2 to about 7.

13. The method of claim 1, wherein said adsorbing is effective to remove at least about 50% by weight of said zirconium complex of the species in said second spent dialysate.

14. The method of claim 1, wherein said adsorbing is effective to remove from about 50% to about 500% by weight of said zirconium complex of the species in said second spent dialysate.

15. The method of claim 1, wherein said ion exchange column is a cartridge comprising at least one of HZO, alkaline anion-exchange material, activated carbon, or any combinations of these layers.

16. The method of claim 1, wherein said ion exchange column is a cartridge comprising alkaline HZO.

17. The method of claim 1, wherein said ion exchange column is a sorbent cartridge.

18. The method of claim 1, wherein said ion exchange column is incorporated into a wearable artificial kidney.

19. The method of claim 1, wherein a dialyzer is provided in fluid communication with at least one treatment station wherein said first spent dialysate passes from said dialyzer to said at least one treatment station where said converting of said species in said first spent dialysate to said adsorbable zirconium complex is provided to produce said second spent dialysate, and then passing said second spent dialysate through said ion exchange column comprising an ion exchange sorbent, wherein the ion exchange column further being in fluid communication with the dialyzer for recirculating at least a portion of said third spent dialysate thereto.

20. The method of claim 19, wherein said first spent dialysate is spent hemodialysate, spent peritoneal dialysate, or combinations thereof.

21. The method of claim 19, wherein said dialyzer is in fluid communication with blood of a patient.

22. An apparatus for conducting dialysis comprising:
a dialyzer in fluid communication with at least one treatment station for passing a first spent dialysate to said at least one treatment station, wherein said first spent dialysate comprising complexable species comprising complexable anions or complexable organic solutes or both;
said at least one treatment station capable of converting said species in said first spent dialysate to adsorbable zirconium polymeric complex anions to produce a second spent dialysate comprising adsorbable zirconium polymeric complex of the species, and said at least one treatment station in fluid communication with an ion exchange column for transmitting said second spend dialysate to said ion exchange column; and
said ion exchange column comprising an ion exchange sorbent through which said second spent dialysate is passable effective for adsorbing at least part of said zirconium polymeric complex of the species from said second spent dialysate on said ion exchange sorbent to produce a third spent dialysate having reduced content of said zirconium polymeric complex of said species than in said second spent dialysate, and wherein the ion exchange column further being in fluid communication with the dialyzer for recirculating at least a portion of said third spent dialysate thereto.

23. A dialysis system comprising:
a dialyzer in fluid communication with at least one treatment station for passing a first spent dialysate to said first treatment station, wherein said first spent dialysate comprising complexable species comprising at least one of complexable anions and complexable organic solutes;
said at least one treatment station capable of converting said species in said first spent dialysate to adsorbable zirconium polymeric complex anions to produce a second spent dialysate comprising adsorbable zirconium polymeric complex of said species, and said at least one treatment station in fluid communication with a sorbent cartridge for passing the second spent dialysate to said sorbent cartridge;
said sorbent cartridge comprising an ion exchange sorbent through which said second spent dialysate is passable effective for adsorbing at least part of said zirconium polymeric complex of the species from said second spent dialysate to produce a third spent dialysate having reduced content of said zirconium polymeric complex of said species than in said second spent dialysate, wherein the sorbent cartridge further being in fluid communication with the dialyzer for recirculating at least a portion of said third spent dialysate thereto.

* * * * *